United States Patent [19]

Kolb et al.

[11] 4,291,585

[45] * Sep. 29, 1981

[54] DEVICE FOR SAMPLING MOLTEN STEEL

[75] Inventors: Gustav Kolb, Garbeck; Friedrich Bardenheuer, Krefeld, both of Fed. Rep. of Germany

[73] Assignees: Mannesmann Aktiengesellschaft, Duesseldorf; Gustav Kolb, Garbeck, both of Fed. Rep. of Germany

[ * ] Notice: The portion of the term of this patent subsequent to Apr. 16, 1996, has been disclaimed.

[21] Appl. No.: 76,450

[22] Filed: Sep. 17, 1979

[30] Foreign Application Priority Data

Sep. 15, 1978 [DE] Fed. Rep. of Germany ....... 2840745

[51] Int. Cl.$^3$ .............................................. G01N 1/12
[52] U.S. Cl. ........................... 73/863.23; 73/864.57; 164/412; 249/DIG. 4
[58] Field of Search ............. 249/DIG. 4; 73/DIG. 9, 73/425.4 R; 164/4, 150, 134, 358, 362, 412

[56] References Cited

U.S. PATENT DOCUMENTS

| 772,720 | 10/1904 | Ladwig | 164/134 X |
| 825,090 | 7/1906 | Turner | 164/134 X |
| 1,049,877 | 1/1913 | Lange | 164/134 X |
| 4,148,221 | 4/1979 | Bardenhever et al. | 73/425.4 R |

FOREIGN PATENT DOCUMENTS 532456 1/1977 U.S.S.R. .............................. 164/358

Primary Examiner—R. L. Spruill
Assistant Examiner—J. Reed Batten, Jr.
Attorney, Agent, or Firm—Smyth, Pavitt, Siegemund & Martella

[57] ABSTRACT

A device for sampling molten steel is provided with a mold cavity and an inlet path which includes a floatation-type slag separation chamber. A ceramic sieve is disposed at the outlet of the separation chamber to prevent large slag particles from passing through while trapping small slag droplets by adhesion.

3 Claims, 2 Drawing Figures

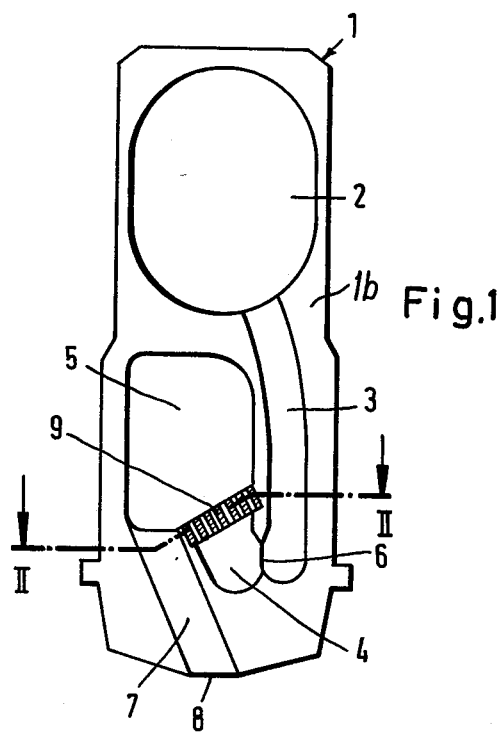
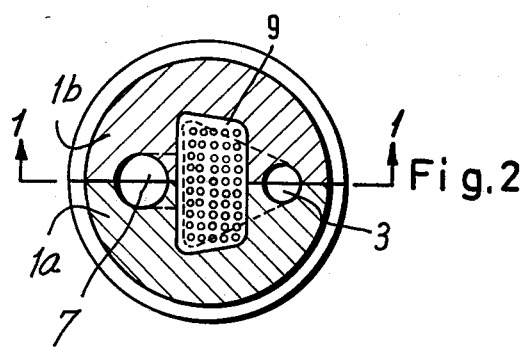

DEVICE FOR SAMPLING MOLTEN STEEL

BACKGROUND OF THE INVENTION

The present invention relates to sampling molten metal, particularly metal, e.g., steel, contained in a vessel and covered by a layer of slag.

During the processing of molten metal, particularly of steel in a blowing converter, one needs to know the particular consistency of the steel during particular and different phases. Therefore, the need arises to take samples from the interior of the bath. Upon taking a sample by means of a probe or sampling device, it is necessary to traverse the slag layer on top so as to introduce the sampling device proper into the interior.

Since the interior content of the converter is to be sampled, entry of slag particles in the sampling device should be avoided, particularly as the device traverses the slag layer. Slag particles should not become embedded in the sample. This problem has not yet been solved satisfactorily.

DESCRIPTION OF THE INVENTION

It is an object of the present invention to provide a new and improved sampling device for molten metal which is constructed to prevent positively slag particles from entering the interior of the sampling device.

It is a more specific object of the present invention to improve the sampling of molten steel from the interior of a blowing converter, with regard to purity of the sample.

It is, therefore, a specific object of the present invention to improve a molten metal sampling device, having a mold cavity and a flow path leading from the exterior to the cavity.

In accordance with the preferred embodiment of the present invention, it is suggested to improve a device such as set forth in the specific object statement above, by placing a ceramic filter into the flow path, to reject larger slag particles and to retain by adhesion small slag droplets, so that slag-free metal flows into the sample mold cavity. It is preferred to set up the flow path for the slag and metal to begin with a duct leading to a floatation-type separation chamber from which a U-shaped outlet duct runs, by way of extension of one leg, to the mold cavity. The ceramic sieve is located right at the junction between the other U-leg and the separation chamber. The separation chamber collects and retains the slag, having low specific density.

DESCRIPTION OF THE DRAWINGS

FIG. 1 is a longitudinal section view through and into a sampling device in accordance with the preferred embodiment of the invention; and FIG. 2 is a section view taken along lines II—II in FIG. 1, and indicating also the section plane (I—I) in which FIG. 1 is taken.

Proceeding now to the detailed description of the drawing, the figures show a sampling body 1 which is longitudinally split and, thus, is constructed from two halves, 1a and 1b. The upper portion contains two matching halves for a mold cavity 2, defining a negative form for the sample to be taken. This mold cavity is located in the neck or upper part of the sampling device which is being stuck into the lower end of a cardboard tube (not shown) by means of which the device is introduced into a bath of molten metal, e.g., steel in a blowing converter.

A duct 3 leads up and to the cavity 2 and serves as an inlet and charge path for the steel to be sampled. This duct is actually also a part of the mold cavity because the steel which will enter and be retained in the duct constitutes a portion of the sample being taken. Duct 3 runs up from one leg of a U-shaped duct portion 4 which includes at its lower portion a slight constriction 6 for establishing a fracture point in the sample.

The short leg of the U-shaped duct portion 4 is the outlet of a separation chamber 5 situated basically underneath cavity 2 and next to duct 3. Chamber 5 has an oblique inlet duct 7, which has an entrance port or mouth piece 8 in the front end or bottom of body 1. Mouth 8 is centrally disposed with respect to the overall contour of body 1, and the bottom in particular.

The short leg of the U-shaped duct, 4, has a rather wide portion adjacent to chamber 5 and narrows towards constriction 6. The wide portion of this duct leg receives a sieve 9 made of a ceramic, i.e., fire-proof material. The sieve is a ceramic body having elongated openings and narrow ducts, which are longer than they are wide.

It can, thus be seen that the flow path for steel runs from opening 8 through duct 7 into chamber 5 and out again through sieve 9, ducts 4 and 3, into sample chamber and mold cavity 2.

The sampling device as described is used and functions as follows. As stated, it is stuck to the lower end of a cardboard tube to be introduced into a bath of molten metal, e.g., steel in a blowing converter. As the sampling device penetrates the slag layer, at least some slag will enter chamber 5 through duct 7. This is true even if opening 8 is closed by a melting cover.

Since slag is lighter than the metal itself, the slag will float towards and gather in the top portion of separation chamber 5. Some slag will, of course, be flushed against sieve 9; however, the particles larger than the apertures of the sieve will not pass through but will, ultimately, be flushed and float towards the upper portion of chamber 5.

Some slag, however, is rather finely divided and small slag droplets will pass into the sieve's apertures. Therefore, the structure of the sieve should be considered. The sieve is actually a ceramic body with a plurality of narrow ducts being considerably longer than wide. Thus, the sieve duct walls do, in fact, trap the slag particles; these droplets will adhere to the sieve duct walls and will thus be retained. On the other hand, steel will not so adhere and is not retained in the sieve ducts.

As a consequence of the foregoing, molten steel will pass through the sieve; but slag droplets are retained by adhesion to the ceramic sieve wall while larger slag particles will be collected in chamber 5. The steel flowing into duct 3 and sample mold cavity 2 is, thus, quite free from slag; a pure metal sample can, thus, be taken.

It is an important aspect of the invention that body 9 is not merely a sieve in the conventional sense; a conventional sieve or mesh permits passage of all particles being smaller than the openings of apertures of the sieve body. Body 9 is, however, a selectively operating trap which permits just some type of material (e.g., molten metal) to pass, while others, e.g. slag, are trapped and adhere to the wall of the sieve ducts. Ultimately, the sieve may clog; but the amount of steel which has to flow through and the period in which steel must flow unimpeded, is quite limited.

The invention is not limited to the embodiments described above, but all changes and modifications thereof not constituting departures from the spirit and scope of the invention are intended to be included.

We claim:

1. Device for sampling molten metal including a body containing a mold cavity and duct means leading from an opening in the body to the mold cavity, the duct means including a first duct connected to the mold cavity, a mixing chamber connected to the first duct and a second duct extending between said opening and the mixing chamber, the improvement comprising a ceramic sieve in the first duct for preventing slag particles from passing through while retaining small slag droplets by adhesion.

2. Device as in claim 1, wherein the sieve is a ceramic body having apertures which are longer than they are wide.

3. Device as in claim 1, the first duct including a main portion communicating with one leg of a U-shaped portion, the other leg being widened at the mixing chamber, the sieve being located in said widened portion.